United States Patent [19]

Castel et al.

[11] Patent Number: 5,188,586
[45] Date of Patent: Feb. 23, 1993

[54] BACK SUPPORT BELT

[75] Inventors: John C. Castel; Dawn S. Castel; Michael R. Hall, all of Topeka, Kans.

[73] Assignee: The Smith Truss Company, Topeka, Kans.

[21] Appl. No.: 771,505

[22] Filed: Oct. 4, 1991

[51] Int. Cl.⁵ .......................... A61F 5/00; A61G 15/00
[52] U.S. Cl. ..................................... 602/19; 128/845
[58] Field of Search .................. 128/845, 78, 874, 875, 128/876, 96.1; 2/44

[56] References Cited

U.S. PATENT DOCUMENTS

| | | | |
|---|---|---|---|
| 1,401,056 | 12/1921 | Doyle | 6.2/19 |
| 1,596,113 | 8/1926 | Monroe | 128/99.1 |
| 1,924,016 | 8/1933 | Barrows | 2/44 |
| 2,282,021 | 5/1942 | Benningfield | 128/100.1 |
| 2,418,009 | 3/1947 | Berman | 2/44 |
| 3,096,760 | 7/1963 | Nelkin | 128/78 |
| 3,393,675 | 7/1968 | Lrznadel et al. | 128/101.1 |
| 3,441,027 | 4/1969 | Lehman | 128/78 |
| 3,452,748 | 7/1969 | Caprio | 602/19 |
| 3,521,623 | 7/1970 | Nichols et al. | 602/13 |
| 3,561,434 | 2/1971 | Kilbey | 128/78 |
| 3,926,183 | 12/1975 | Spiro | 128/78 |
| 4,022,197 | 5/1977 | Castiglia | 602/61 |
| 4,135,503 | 1/1979 | Romano | 128/78 |
| 4,175,553 | 11/1979 | Rosenberg | 128/78 |
| 4,245,628 | 1/1981 | Eichler | 128/78 |
| 4,269,179 | 5/1981 | Burton | 128/78 |
| 4,993,409 | 2/1991 | Grim | 128/78 |

OTHER PUBLICATIONS

Pro Flex Brochure; CR 1988; Ergodyne Corp.; St. Paul, Minn.
Physical Therapy; vol. 71, No. 6, p. 143; Jun. 1991.
Orthopedic Product Catalog; D. Smith Truss Co.; Topeka, Kans., CR 1990.

Primary Examiner—Robert A. Hafer
Assistant Examiner—Michael Brown
Attorney, Agent, or Firm—Litman, McMahon & Brown

[57] ABSTRACT

A back support brace for supporting the back of a wearer of the brace for preventing injuries and reinforcing proper lifting mechanics during lifting activities comprises a back panel, a left side panel and a right side panel wherein the left and right side panels are secured at opposite ends of the back panel and are wrappable around the waist of a wearer and adjustably securable thereto. Aligned pairs of belt loops are provided on an inner surface of the brace and are adapted to receive a belt for holding up the pants of the wearer of the brace therethrough so as to prevent the brace from being advanced out of a preset position during lifting activities. A lower edge of the brace includes cutout portions generally positioned above the thighs of the wearer such that the lower edge is contoured to conform to the shape of the wearer throughout lifting activities. Elastic insets extend over the cutout portions to increase tension across the back panel.

17 Claims, 2 Drawing Sheets

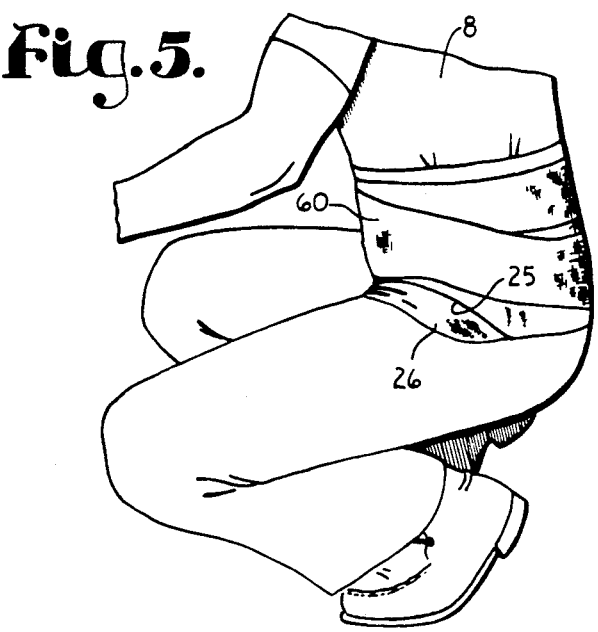
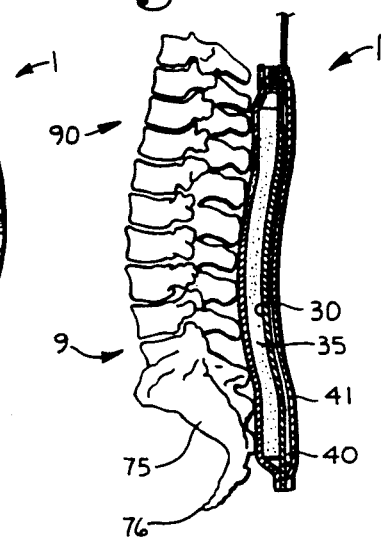
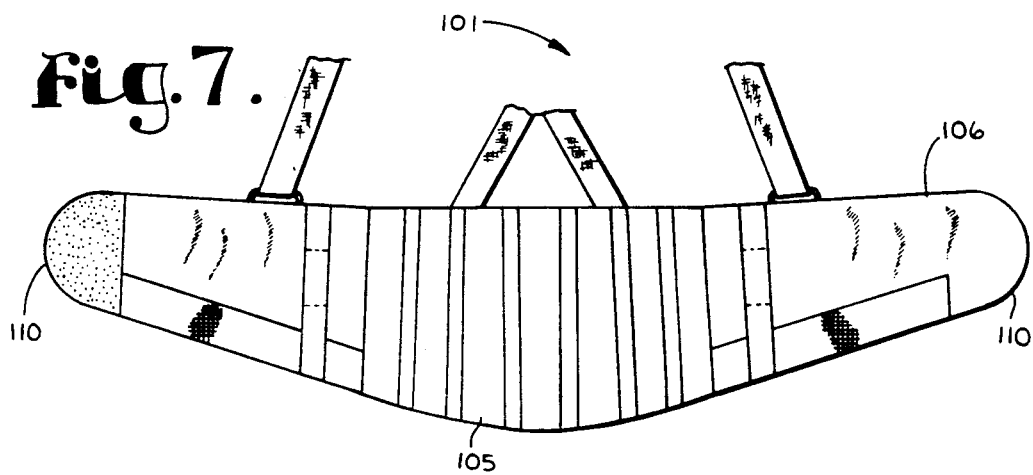
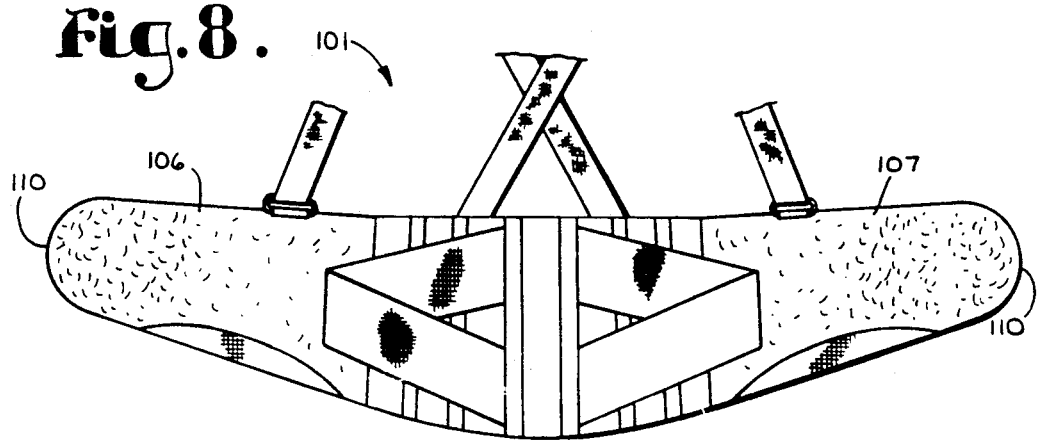

ized at approximately one hundred billion dollars per year. It is estimated that each year nearly half a million workers are permanently sidelined by back injuries. Lower back pain and back injuries account for nearly forty percent of all work days missed, resulting in over 93 million lost work days per year. Most lower back injuries and lower back pain result from improper lifting mechanics or techniques. Many of the injuries that occur can be prevented by proper lifting techniques; however, even with training in proper techniques, many workers fail to use such techniques and become injured.

BACK SUPPORT BELT

BACKGROUND OF THE INVENTION

The present invention generally relates to a back support belt to be worn by a worker to reduce the risk of back injury during lifting activities.

Back injuries are a very costly health problem for industry. Some estimates place the total cost of back injuries to industry in the United States at approximately one hundred billion dollars per year. It is estimated that each year nearly half a million workers are permanently sidelined by back injuries. Lower back pain and back injuries account for nearly forty percent of all work days missed, resulting in over 93 million lost work days per year. Most lower back injuries and lower back pain result from improper lifting mechanics or techniques. Many of the injuries that occur can be prevented by proper lifting techniques; however, even with training in proper techniques, many workers fail to use such techniques and become injured.

It has been found that provision of additional support to the backs of workers through the use of belts, braces or wraps can considerably reduce back injuries, perhaps both because such devices provide added support and because such devices may encourage and remind the worker to use better technique. Such belts, braces or wraps appear to provide support by compressing the tissue around the spine so as to stabilize the lumbar spine and prevent substantial lateral motion of the vertebrae thereof relative to one another which may otherwise occur and cause painful injury.

As noted, many such belts, braces or wraps have also been designed to reinforce proper lifting techniques. When lifting heavy objects, it is preferred to use the legs as much as possible to perform the lift. To insure that the legs are doing most of the lifting as opposed to the back, the lift should begin with the lifter in a squatting position with the back aligned within 45 degrees of vertical. However, individuals often lift items with the back aligned 45-90 degrees beyond vertical such that the back bears most of the load during lifting. Many braces incorporate features which make it uncomfortable for a wearer to bend their back more than 45 degrees from vertical, thereby reinforcing proper lifting techniques.

Numerous back support belts or braces have been designed to be worn under the garments of a wearer. These belts often trap in body heat and become uncomfortable to wear in a warm environment. Also, it is extremely inconvenient for the wearer to remove the belt if the wearer has to remove the brace at various times during their work period. Such removal requires the wearer to remove and then put back on their regular clothing in order to remove the belt or brace.

Certain prior art back support belts or braces have been designed for wearing over the clothes of a wearer. A significant shortcoming of currently available overwrap and underwrap support belts is that these belts tend to be pushed upwards out of proper support position during use by a wearer. To provide maximum back support, the back support belt should provide support through the lower back down to the upper portion of the sacrum. With currently available back support belts, as a lifter squats down to pick up an object the lifter's thighs engage a lower edge of the belts so as to urge the belt upwards. After several lifts, these belts no longer provide support for the back as far down the back as is preferred. Furthermore, such belts are difficult to correctly position, whether the belt has simply slipped out of place or when retightening after the belt has been released for some reason.

SUMMARY OF THE INVENTION

The present invention provides a back support belt or brace for reducing the risk of lower back injury. The brace generally comprises a back panel, a left side panel and a right side panel. The back panel is constructed of a flexible elastic material. The outer surfaces of both the left side panel and the right side panel include variable position fastening means such as appropriate portions of a hook and loop fastening system. Another portion of the hook and loop fastening system is secured to a radially inward facing surface of the right side panel near an outer end thereof.

When putting on the back support brace the wearer initially places an inner surface of the back panel in abutting relationship with their back. The wearer then wraps the left side panel around the left and front portion of the wearer's waist. Then the wearer wraps the right side panel around the right and front portion of the waist and engages the hook and loop fastening portions of the left side panel and the inner surface of the right side panel so as to secure the brace in position. The brace should fit relatively snugly against the wearer. A lower edge of the back panel of the brace should extend down the back so as to cover the sacrum to the point where the sacrum curves inward.

The snugness or fit of the brace can be controlled using first and second tensioning pulls which are secured to the back panel and extend over the left side panel and right side panel respectively. The relative positioning of the pulls may be adjusted to increase or decrease the compressive forces of the belt on the wearer. An alternative back support pad is insertable in a pouch in the back panel to provide greater support for the lumbosacral area of the back.

When worn externally, the brace includes a set of suspenders such that a wearer of the back support brace may unfasten the brace during breaks or when not lifting without having to fully remove the brace. A plurality of stays are secured to the back panel in vertical and spaced relationship to provide stiffness to the back panel.

A set of alternative belt loops; preferably including an upper, a middle and a lower belt loop are secured to the inner surface of both the left side panel and the right side panel. When putting on the back support brace, the wearer threads the belt for holding up his or her pants through a selected one of the belt loops on the left side panel and a corresponding belt loop on the right side panel. When the back support brace is subsequently secured in place with the hook and loop-type fastener on the left and right side panels, the belt loops cooperate with the wearer's belt to prevent the back support brace from advancing upwards relative to the wearer's pants so as to maintain the back support brace in the proper, preselected position throughout use and also properly position the belt for fastening, such that the user can quickly resecure the belt after loosening.

The left and right side panels include a cutout portion extending along a lower edge of each of the side panels so as to be located at the tops of each thigh of the user. An elastic inset extends across the cutout portion of both the left side panel and the right side panel. The cutout portions allow the user to bend the users legs into a squatting position without substantial resistance from the belt and help prevent the brace from being pushed upwards by the thighs of the wearer when the wearer squats down into a squatting position. The elastic insets stretch in response to engagement with the thigh of the wearer but continue to transfer tension across the lower portion of the back support brace to help support the lower end of the back even when the user is squatting.

OBJECTS AND ADVANTAGES OF THE INVENTION

Therefore, the objects of the present invention are: to provide a device for providing support to the lower back of a wearer; to provide such a device which reinforces and encourages proper lifting techniques; to provide such a device which can be worn on top of or outside the regular working clothes of a wearer; to provide such a device which is easy to transfer between working and non-working configurations on a user; to provide such a device which is relatively lightweight; to provide such a device which is readily releasable; to provide such a device wherein the amount of support provided is adjustable; to provide such a device which does not advance upward relative to the wearer during use; to provide such a device that is relatively inexpensive to manufacture, easy to use and particularly well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 5 is a perspective view of the back support brace of the present invention shown in position on a wearer who is positioned in a squatting position.

FIG. 6 is a cross-sectional view taken along line 6—6 of FIG. 3.

FIG. 7 is a front elevational view of a modified back support brace according to the present invention.

FIG. 8 is a rear elevational view of the modified back support.

DETAILED DESCRIPTION OF THE INVENTION

Figure 1:
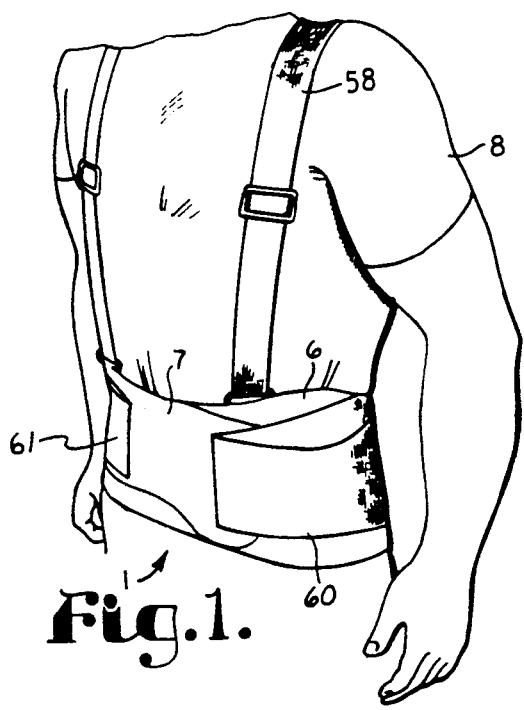
FIG. 1 is a perspective view of a back support brace according to the present invention secured in support position on a wearer.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally represents a back support brace, belt or wrap according to the present invention. The back support brace 1 comprises a back panel or back section 5, a left side panel, left side section or left wing 6 and a right side panel, right side section or right wing 7. The back panel 5 is generally rectangular and preferably constructed of a pliable and flexible, woven elastic material. The back panel 5 is designed to generally extend across the lower back of a wearer 8 and more specifically the lumbosacral region 9 of the back.

Figure 3:
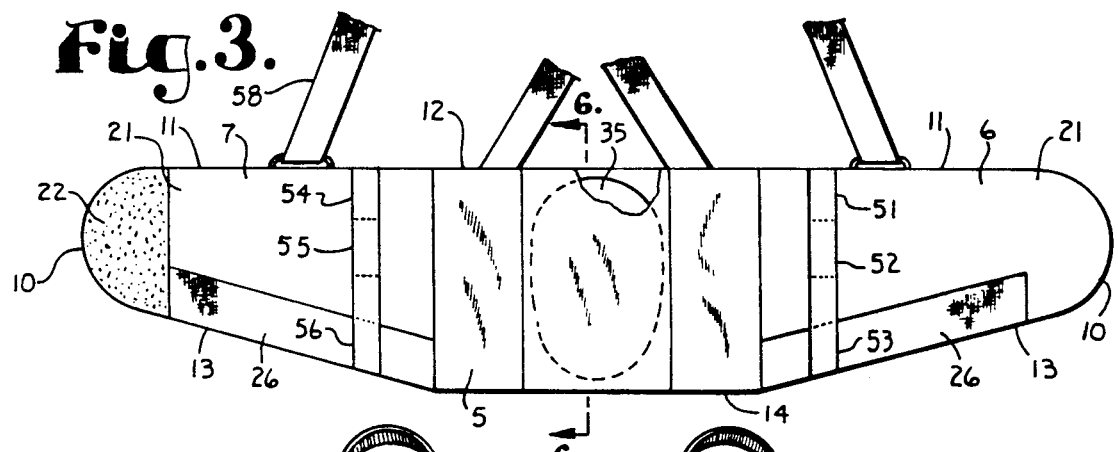
FIG. 3 is a front elevational view of the back support brace with portions broken away to show a support pad within a pocket in the back support brace.
Figure 4:
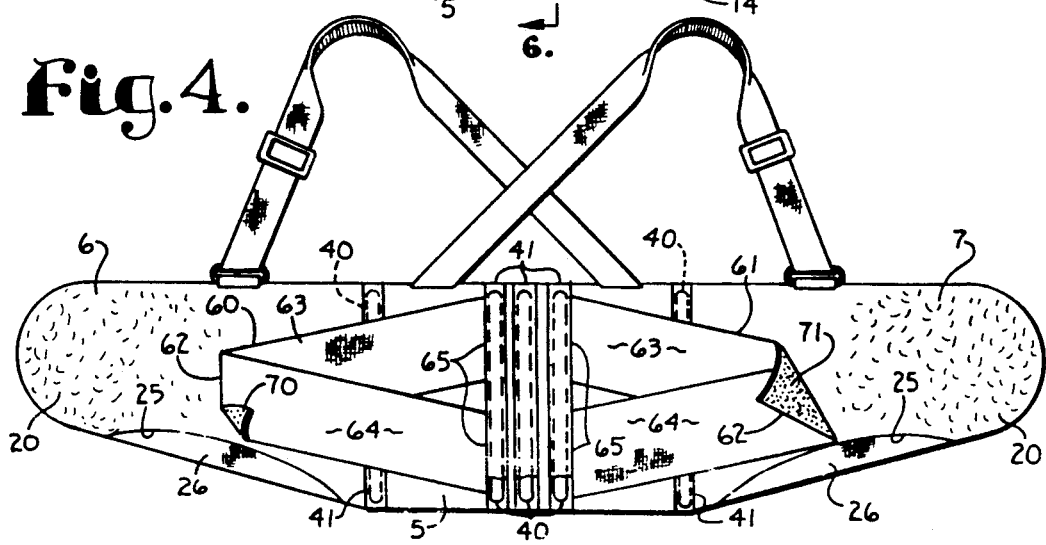
FIG. 4 is a rear elevational view of the back support brace with portions broken away to show stays within stay receiving sleeves.

The left side panel 6 and the right side panel 7 are somewhat triangularly shaped having a rounded outer edge 10. An upper edge 11 of both the left side panel 6 and the right side panel 7 extends in linear alignment with an upper edge 12 of the back panel 5, when the brace 1 is in an open position such as is shown in FIG. 3. Lower edges 13 of the left side panel and the right side panel extend upward away from a lower edge 14 of the back panel 5 towards respective outer corners 10 such that the widest part of the brace 1 is along the back panel 5.

The left side panel 6 and the right side panel 7 have an outer surface 20 and an inner surface 21. The outer surface 20 of both the left side panel 6 and the right side panel 7 is constructed of a first type of material forming a hook and loop type fastener as is sold under the trademark Velcro. A first section 22 of a second type of material forming a hook and loop type fastener is secured to the inner surface 21 of the right side panel 7 adjacent the rounded outer corner 10 thereof. The first section 22 of the second type of material of a hook and loop fastener is adapted to engage and fasten to the first type of material of a hook and loop type fastener forming the outer surface 20 of the left side panel 6 to secure the back support brace 1 in encircling relationship around a wearer as shown in FIG. 1.

The lower edges 13 of the left and right side panels 6 and 7 are contoured or curved inward (upward when in use) with respect to the left and right side panels 6 and 7 so as to form a cutout portion 25 in the left side panel 6 and the right side panel 7. The cutout portions 25 are designed to better conform to the shape of a wearer of the brace 1 as will be discussed in greater detail below. Elastic insets 26 made of a woven elastic material are secured to the inner surfaces 21 of the left and right side panels 6 and 7 so as to extend over or across the cutout portions 25. The cutout portions 25 in conjunction with the elastic insets 25 allow a user's upper thighs to flex with respect to hips, as seen in FIG. 5, without substantially pushing the brace 1 upward.

The back panel 5 of the brace 1 is constructed of two layers of woven elastic material, sewn together to form a pocket 30 having an opening 31 along the upper edge 12 of the back panel 5. A support pad or insert 35 is removably insertable within the pocket 30. The support pad 35 is preferably ovate and constructed of a flexible, polylaminate material, such as 2.2 pound polyethylene foam. The pocket 30 includes a closure or fastening means as shown by the fastener 36 in FIG. 5 to secure the pad 35 within the pocket 30. The fastener 36 is preferably a hook and loop type fastener.

Five stays 40 are secured to the back panel 5 and generally extend from the lower edge 14 to the upper edge 12 of the back panel 5 in spaced relationship. The flexible stays 40 are constructed of a material having a greater rigidity than the woven elastic material of the back panel 5 but flexible enough to flex with the back of wearer of the brace 1 while in use. The preferred stays 40 are referred to as spiral stays, comprising coiled and flattened spring steel round wire such as a product sold under the trademark Higgins Spiral Boning. The stays 40 are secured to the back panel 5 in stay receiving sleeves 41. The stays 40 may be removably enclosed or nonremovably enclosed in the stay receiving sleeves 41. The stays 40 help to provide stiffness to the back panel 5 but allow the back panel to flex to conform the shape of the back of the wearer.

First, second and third left side belt loops 51, 52 and 53 are formed on the inner surface 21 of the left side panel 6 so as to generally extend in linear alignment from near a lower edge 13 to near an upper edge 11 of the left side panel 6. First, second and third right side belt loops 54, 55 and 56 are formed on the inner surface 21 of the right side panel 7 so as to generally extend in linear alignment from near a lower edge 13 to near an upper edge 11 of the right side panel 7. The first, second and third left side belt loops 51, 52 and 53 are horizontally aligned with the first, second and third right side belt loops 54, 55 and 56 respectively, when the brace 1 is in use and the user is standing erect.

A set of suspenders 58 are secured to the back support brace 1 along the upper edges 12 and 11 of the left and right side panels 6 and 7 and the back panel 5. The suspenders 58 are preferably made of a woven elastic material and are length or size adjustable.

A first tensioning pull 60 and a second tensioning pull 61 are secured at one end thereof to the back panel 5 near the center thereof and allow a wearer to adjust the tension, compression or snugness of fit of the brace 1 so as to increase or decrease the amount of support provided by the brace 1 by manipulation of an opposite movable and attachable end of each. Each of the pulls 60 and 61 is formed of a strip of woven elastic material bent over in half along a fold line at a distal end 62 to form a first and a second leg 63 and 64. The legs 63 and 64 are angled apart from each other in the shape of a V. In particular, proximate ends 65 of the legs 63 and 64 are secured to the back panel 5 on an outer surface thereof such that the first and second tensioning pulls 60 and 61 extend over the left and right side panels 6 and 7 respectively. A second and a third section 70 and 71 of the second portion of a hook and loop fastener are secured on an underside of the first and second tensioning pulls 60 and 61 respectively adjacent respective distal ends 62. The second and third sections 70 and 71 of the second or portion of the hook and loop fastener hook material engage and secure to the first type of material of a hook and loop fastener forming the outer surface 20 on the left and right side panels 6 and 7 to adjustably secure the first and second tensioning pulls 60 and 61 thereto and thereby allow the brace 1 to be easily donned and/or tension adjusted.

Figure 2:
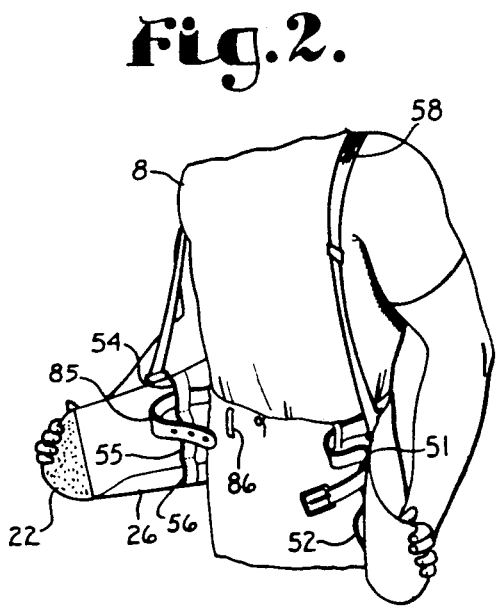
FIG. 2 is a perspective view of the back support brace on a reduced scale showing the back support brace being secured to a wearer.

The back support brace 1 is generally constructed of light weight, woven, breathable materials and is designed to be worn over the regular work clothes of a wearer during lifting activities. To put on the brace 1, the wearer initially inserts his or her arms through the suspenders 58 such that the suspenders 58 support the brace 5 at about waist level of the wearer as shown in FIG. 2. The lower edge 14 of the back panel 5 should be positioned so as to generally extend across the sacrum 75 of the wearer just above the coccyx 76 as shown in FIG. 5. The left side panel 6 should be positioned on the wearer's left and the right side panel 7 should be positioned on the wearer's right. The wearer then threads a belt 85 for his or her pants through the aligned left and right side belt loops 51 and 54, 52 and 55, or 53 and 56 that are adjacently aligned with the belt 85 while also threading the belt 85 simultaneously through the belt loops 86 associated with the pants, as is shown in FIG. 2.

The left and right side belt loops 51 and 54, 52 and 55, or 53 and 56 selected for use will depend on the desired positioning by the wearer. It is foreseen that the belt loops 51, 52, 53, 54, 55 and 56 may include fastening means, not shown, such that each belt loop 51, 52, 53, 54, 55 and 56 may be opened and then closed to receive or encircle the belt 85 of the wearer such that the wearer of the brace 1 does not have to unfasten their belt 85 from their pants, thread their belt through the belt loops 51 and 54, 52 and 55, or 53 and 56 in the brace 1, thread the belt 85 back through the belt loops 86 in the wearer's pants and then refasten the belt 85.

After threading the belt 85 through belt loops 51 and 54, 52 and 55, or 53 and 56 and fastening the belt in place, the wearer then wraps the left side panel 6 across his or her abdomen for a relatively snug fit. The right side panel 7 is then wrapped around the abdomen of the wearer so as to be positioned over the left side panel 6 such that the brace 1 completely encircles the waist of the wearer. The right side panel 7 is pressed against the outer surface 20 of the left side panel 6 such that the first section or portion 22 of hook and loop type material on the inner surface 21 of the right side panel 7 engages the hook and loop portion of the left side panel 6 so as to securely fasten the right side panel 7 to the left side panel 6.

The brace 1, secured around the waist of a wearer provides support for the back by compressing or restricting movement of the tissue therebetween so as to provide greater stability to the spine. The first and second tensioning pulls 60 and 61 are operable to vary the tension therein or radial compressive force or support applied to the wearer's back or spine. To increase the tension, the wearer grasps either or both of the tensioning pulls 60 and 61 at the distal ends 62 thereof, unfastens the distal ends 62 of the tensioning pulls 60 and 61 from the left an right side panels 6 and 7 by pulling radially outward, stretches the tensioning pulls 60 and 61 away from their respective proximate ends 65, and refastens the tensioning pulls 60 and 61 to the left and right side panels 6 and 7 using the second and third sections 70 and 71 of hook and loop type material secured to the tensioning pulls 60 and 61 respectively. The distal end 62 of the first tensioning pull 60 may be secured to the hook and loop type material on the outer surface 20 of either the left side panel 6 or the right side panel 7. Similarly, the distal end 62 of the second tensioning pull 61 may be secured to the hook and loop type material on the outer surface 20 of either the right side panel 7 or the left side panel 6. To reduce the tension of the brace I on the wearer, the tensioning pulls 60 and 61 are unfastened and the natural resiliency of the elastic material forming the tensioning pulls 60 and 61 is allowed to contract the tensioning pulls 60 and 61 which are then refastened to the left and right side panels 6 and 7 respectively.

When additional support for the wearer's back is desired, the brace 1 is worn with the support pad 35 inserted in the pocket 30 in the back panel 5. The pocket 30 is located in the back panel 5 such that the support pad 35 may be positioned so as to extend over the lumbosacral region 9 of the spine. With the support pad 35 in place and the brace 1 adjusted to fit snugly about the wearer, the support pad 35 flexes to conform to the shape of the back throughout lifting activities.

It is foreseen that the support pad 35 may include heat transfer means for heating or cooling the area of the back covered by the support pad 35 if so desired. More specifically, the support pad 35 may comprise a sealed plastic bag containing a liquid or fluid. The contents of the bag may be cooled by placing the bag in a refrigerator or freezer or heated using a microwave oven. After heating or cooling, the bag is placed in the pocket 30 to heat or cool the area of the back covered by the support pad 35 when the brace 1 is in use.

It is also foreseen that the support pad 35 may be made of a deformable material such that the support pad 35 could initially be deformed to conform to the shape of the region of the back where the support pad 35 is to be applied, preferably the lumbosacral region of the back. The shape could then be set such that the support pad 35 would generally be inflexible. Heat deformable thermoplastics could be used for such a deformable support pad 35. Initially the heat deformable material is heated so that the material is deformable and then the material is molded or shaped to conform to the lumbosacral region of the back when the wearer's back is in an upright or generally vertical position or alignment. The material is then be cooled so as to set the material in the molded form. The molded support pad 35 is then inserted in the pocket 30 of the brace 1 for additional support.

While wearing the brace 1 a wearer may unfasten the right side panel 7 from the left side panel 6 without having to take the brace off completely and set it down because the brace 1 will be supported in position by the suspenders 58 and by the wearers belt 85 threaded through the left and right side belt loops 51 and 54, 52 and 55, or 53 and 56. The brace 1 may be unfastened so as to be supported by the suspenders 58 during breaks, to cool off or to reduce the compressive forces on the wearer's abdomen.

As discussed above, the lower edge 14 of the back panel 5 should be positioned so as to extend across the sacrum 75 just above the coccyx 76 of the wearer. More specifically, the lower edge 14 of the back panel 5 is preferably positioned so as to extend across the portion of the sacrum 75 wherein the sacrum 75 begins to curve inward just above the coccyx 76. The upper edge 12 of the back panel 5 should extend just above the lumbar portion 90 of the spine. To prevent the brace 1 from being advanced upward and out of proper position by the engagement of the thighs of the wearer against the lower edges 13 of the left and right side panels 6 and 7 as the wearer squats and to allow greater flexibility in the legs of the user, the cutout portions 25 and the aligned left and right side belt loops 51 and 54, 52 and 55, or 53 and 56 function as means for preventing upward displacement of the brace 1. The cutout portions 25 reduce upward displacement of the brace 1 by effectively allowing the lower edge 13 of the left and right side panels 6 and 7 to flex upward such that when the wearer of the brace 1 squats into a squatting position the lower edge 13 of both the left and right side panels 6 and 7 along the cutout portions 25 extends just above the upper surface of the wearers thighs at the hip. The elastic insets 26, which extend across the cutout portions 25, stretch or give to conform to the thigh but still provide tension across the lower edges 13 of the left and right side panels 6 and 7 to ensure that a lower portion of the back panel remains snugly pressed against the back of the wearer generally across the sacrum 75. The aligned left and right side belt loops 51 and 54, 52 and 55, or 53 and 56 having the belt 85 of a wearer threaded therethrough also operate to prevent the brace 1 from being urged upwards during use.

The back support brace 1, when snugly secured to a wearer, reinforces proper lifting techniques by discouraging a wearer of the brace 1 from bending their back more than approximately 45 degrees from vertical. If the wearer of the brace 1 bends their back too far the lower edges 13 of the left and right side panels 6 and 7 dig into the abdomen just below the brace 1 making it uncomfortable for the wearer to bend that far. The stiffness of the back panel 5 provided by the stays 40 and in part by the support pad 35, particularly a support pad 35 made of a rigid material molded to conform to the shape of the back, also restricts the ability of the wearer to bend their back more than 45 degrees beyond vertical. Because the brace 1 discourages the wearer from bending over, the wearer must squat down with a relatively straight back to grasp an item to be lifted from a lower level as shown in FIG. 6. This encourages the wearer of the brace 1 to use their legs during lifting and not their back.

A modified back support brace in accordance with the present invention is shown in FIGS. 7 and 8 and is generally designated by the reference numeral 101. Many of the characteristics of the modified brace 101 are substantially similar to those previously described for the brace 1 and will not be reiterated here in detail. The brace 101 includes a back section 105, a left side section or left wing 106 and a right wing or right side section 107. Opposite ends 110 of the brace 1 are rounded and an upper edge 111 of the brace 101 is generally linear when not in use and in a single plane when in use. A lower edge 113 of the brace 101 is curved downward such that the widest portion of the brace 101 is at the center of the back section 105.

The back section 105 is preferably constructed of a lightweight, breathable material such as the material sold under the trademark Lycra Powernet. The material is preferably woven into a stretchable net or web providing support and ventilation to the back while allowing the back section 105 to conform to the shape of the wearer's back and to allow for slight expansion and contraction of the back section 105.

It is to be understood that while certain forms of the present invention have been illustrated and described herein, it is not to be limited to the specific forms or arrangement of parts described and shown.

What is claimed and desired to be secured by Letters Patent is as follows:

1. A brace for preventing back injuries to a wearer of the brace during lifting activities; said brace comprising:
   (a) a back section adapted to generally extend across the lumbosacral region of the back of the wearer;
   (b) a left side section and a right side section secured to opposite ends of said back section such that said left side section is adapted to extend around the left side of the wearer and the right side section is adapted to extend around the right side of the wearer during use;

(c) adjustable fastening means for adjustably fastening said left side section to said right side section such that said brace encircles the wearer and such that the fit of the brace with respect to the wearer may be adjusted;

(d) at least one belt loop secured to an inner side of said brace during use and adapted to receive a pant supporting belt worn by a wearer of the brace for preventing said brace from being substantially advanced upward out of a preselected position; and (e) a lower edge of said left and right side sections being contoured so as to form a cutout portion in the left side section and the right side section; each of said cutout portions adapted to conform to the shape of an upper leg of a wearer in a squatting position.

2. A brace according to claim 1 including:
(a) an elastic inset extending across the cutout portions of the left and right side sections.

3. The brace as described in claim 1 wherein:
(a) said belt loop is a left side belt loop secured to an inner surface of said left side section; and said brace further includes
(b) a right side belt loop secured to an inner surface of said right side section such that said right side belt loop is aligned with said left side belt loop and said left and right side belt loops are adapted to receive the pant belt of the wearer of the brace.

4. A brace as described in claim 1 further comprising:
(a) a set of suspenders secured to said brace.

5. The brace as described in claim 1 wherein:
(a) said back section is constructed of elastic material.

6. The brace as described in claim 1 including:
(a) a pocket formed in said back section of said brace with a support pad removably securable within said pocket.

7. The brace as described in claim 1 including:
(a) a plurality of elongate stays secured to said back section of said brace for stiffening said back section.

8. The brace as described in claim 7 wherein said tensioning means comprise:
(a) a first tensioning pull made of elastic material and having a distal end and a proximate end; said proximate end of said first tensioning pull secured to said back section; said distal end of said first tensioning pull removably securable to selective multiple positions along said left side section such that said first tensioning pull may be stretched therebetween; and
(b) a second tensioning pull made of elastic material and having a distal end and a proximate end; said proximate end of said second tensioning pull secured to said back section; said distal end of said second tensioning pull removably securable to selective multiple positions along said right side section such that said second tensioning pull may be stretched therebetween.

9. The brace as described in claim 1 including:
(a) tensioning means for selectively adjusting the brace relative to a wearer.

10. A brace for preventing back injuries to a wearer of the brace during lifting activities; said brace comprising:
(a) a back section adapted to generally extend across the back of the wearer of the brace;

(b) a left side section and a right side section secured to opposite ends of said back section such that said left side section is adapted to extend around the left side of the wearer and the right side section is adapted to extend around the right side of the wearer when in use;

(c) adjustable fastening means for adjustably fastening said left side section to said right side section such that said brace encircles the wearer and such that the fit of the brace with respect to the wearer may be adjusted;

(d) a left side belt loop secured to an inner surface of said left side section and a right side belt loop secured to an inner surface of said right side section such that said right side belt loop is aligned with said left side belt loop and said left and right side belt loops are cooperatively positioned on the inner side of said brace so as to be adapted to receive a clothing belt worn by the wearer of the brace;

(e) a lower edge of said left and right side sections being contoured so as to form a cutout portion in the left side section and the right side section; each of said cutout portions being adapted to conform to the shape of an upper leg of a wearer of the brace positioned in a squatting position;

(f) a pocket formed in said back section of said brace;

(g) a support pad removably secured within said support;

(h) a plurality of stays secured to said back section of said brace for stiffening said back section;

(i) tensioning means for selectively adjusting a compressive force of the brace against a wearer; and (j) a set of shoulder supporting suspenders secured to said brace.

11. The brace according to claim 10 including:
(a) left and right elastic insets extending across each of said cutout portions respectively.

12. The brace as described in claim 10 wherein:
(a) said back section is constructed of elastic material.

13. The brace as described in claim 10 wherein said tensioning means comprise:
(a) a first tensioning pull made of elastic material and having a distal end and a proximate end; said proximate end of said first tensioning pull secured to said back section; and said distal of said first tensioning pull removably securable to selective multiple positions along said left side section such that said first tensioning pull may be stretched therebetween; and
(b) a second tensioning pull made of elastic material and having a distal end and a proximate end; said proximate end of said second tensioning pull secured to said back section; and said distal of said second tensioning pull removably securable to selective multiple positions along said right side section such that said second tensioning pull may be stretched therebetween.

14. In a brace for preventing back injuries to a wearer of the brace during lifting activities wherein said brace is generally nonelastic and positioned to encircle a user at the lower back during use, the improvement comprising:
(a) left and right lower cutout portions in said brace adapted to be located so as to allow a user's upper legs to flex during squatting without forcing said belt upward; and
(b) left and right elastic insets across said left and right cutout portions respectively, transferring tension in the lower end of said brace between opposite sides of said cutout portions.

15. A brace for preventing back injuries to a wearer of the brace during lifting activities; said brace comprising:
   (a) a back section adapted to generally extend across the lumbosacral region of the back of the wearer;
   (b) a left side section and a right side section secured to opposite ends of said back section such that said left side section is adapted to extend around the left side of the wearer and the right side section is adapted to extend around the right side of the wearer during use;
   (c) adjustable fastening means for adjustably fastening said left side section to said right side section such that said brace encircles the wearer and such that the fit of the brace with respect to the wearer may be adjusted;
   (d) at least one belt loop secured to said brace and adapted to receive a pant supporting belt worn by a wearer of the brace for preventing said brace from being substantially advanced upward out of a preselected position;
   (e) a lower edge of said left and right side sections being contoured so as to form a cutout portion in the left side section and the right side section; each of said cutout portions adapted to conform to the shape of an upper leg of a wearer in a squatting position;
   (f) said left side belt loop is a first left side belt loop and said brace further includes a second left side belt loop and a third left side belt loop secured to an inner surface of said left side section between a lower edge and an upper edge of the left side portion; and
   (g) said right side belt loop is a first right side belt loop and said brace further includes a second right side belt loop and a third right side belt loop secured to an inner surface of said right side section between a lower edge and an upper edge of the right side section; said first left side belt loop, said second left side belt loop and said third left side belt loop aligned with said first right side belt loop, said second right side belt loop and said third right side belt loop respectively so as to be adapted to cooperatively receive the belt of the wearer of the brace at different levels along the brace.

16. A brace for preventing back injuries to a wearer of the brace during lifting activities; said brace comprising:
   (a) a back section adapted to generally extend across the back of the wearer of the brace;
   (b) a left side section and a right side section secured to opposite ends of said back section such that said left side section is adapted to extend around the left side of the wearer and the right side section is adapted to extend around the right side of the wearer during use;
   (c) adjustable fastening means for adjustably fastening said left side section to said right side section such that said brace encircles the wearer and such that the fit of the brace with respect to the wearer may be adjusted;
   (d) a left side belt loop secured to an inner surface of said left side section and a right side belt loop secured to an inner surface of said right side section such that said right side belt loop is aligned with said left side belt loop and said left and right side belt loops are adapted to receive a clothing belt worn by the wearer of the brace;
   (e) a lower edge of said left and right side sections being contoured so as to form a cutout portion in the left side section and the right side section; each of said cutout portions being adapted to conform to the shape of an upper leg of a wearer of the brace positioned in a squatting position;
   (f) a pocket formed in said back section of said brace;
   (g) a support pad removably secured within said support;
   (h) a plurality of stays secured to said back section of said brace for stiffening said back section;
   (i) tensioning means for selectively adjusting a compressive force of the brace against a wearer;
   (j) a set of shoulder supporting suspenders secured to said brace;
   (k) said left side belt loop is a first left side belt loop and said brace further includes a second left side belt loop and a third left side belt loop secured to an inner surface of said left side section between a lower edge and an upper edge of the left side section; and
   (g) said right side belt loop is a first right side belt loop and said brace further includes a second right side belt loop and a third right side belt loop secured to an inner surface of said right side section between a lower edge and an upper edge of the right side section; said first left side belt loop, said second left side belt loop and said third left side belt loop aligned with said first right side belt loop, said second right side belt loop and said third right side belt loop respectively so as to be adapted to cooperatively receive the clothing belt worn by the wearer of the brace at different levels along the brace.

17. In a back brace that is adapted to be selectively positionable so as to encircle a wearer so as to extend across a portion of the wearer's back for use by a wearer in preventing back injuries during lifting activities, the improvement comprising:
   (a) position maintaining means located on said brace so as to be adopted to cooperatively engage underlying clothing of a user for releasably securing said brace to the clothing so as to prevent said brace from being urged upward and out of a preselected position during use;
   (b) cutout portions in a left side section and a right side section of said brace extend upward from a lower edge of said brace; each of said cutout portions is connected to be adapted to conform to the shape of upper thighs of a wearer of the brace positioned in a squatting position; and
   (c) elastic insets secured to said brace so as to extend across said cutout portions.

* * * * *